United States Patent [19]

Jäger et al.

[11] 4,277,557
[45] Jul. 7, 1981

[54] PHOTOGRAPHIC MATERIAL CONTAINING A STABILIZING AGENT

[75] Inventors: Gerhard Jäger, Wuppertal; Anita von König, Krefeld; Werner Liebe, Leverkusen; Armin Voigt, Cologne, all of Fed. Rep. of Germany

[73] Assignee: AGFA-Gevaert, A.G., Leverkusen, Fed. Rep. of Germany

[21] Appl. No.: 968,269

[22] Filed: Dec. 11, 1978

[30] Foreign Application Priority Data

Dec. 15, 1977 [DE] Fed. Rep. of Germany ....... 2756030

[51] Int. Cl.$^3$ ............................................... G03C 1/34
[52] U.S. Cl. .................................... 430/446; 430/454; 430/463; 430/551; 430/607; 430/613; 430/614; 430/615
[58] Field of Search ....................... 96/66.5, 109, 66.4, 96/66.3, 95, 114.1; 430/489, 490, 551, 607, 614

[56] References Cited

U.S. PATENT DOCUMENTS

| | | | |
|---|---|---|---|
| 3,147,118 | 9/1964 | Dersch et al. | 96/109 |
| 3,212,900 | 10/1965 | Oguchi | 430/607 |
| 3,707,377 | 12/1972 | Van Dyke Tiers et al. | 96/109 |
| 3,837,863 | 9/1974 | Sakazume et al. | 96/109 |
| 4,066,461 | 1/1978 | Shimamura | 96/66.4 |
| 4,108,665 | 8/1978 | Gutman et al. | 96/114.1 |

OTHER PUBLICATIONS

Kuwabara, "Effects of Acetylene Derivatives on Photographic Emulsions", Bulletin of the Society of Scientific Photography of Japan, No. 16, Dec. 1966, pp. 13–23.

C. A. 78:166425c, Infrared Spectra of Methyl-d$_2$ Chloride and Propyne 3,3-d$_2$ and Geometries of Methyl Chloride and Propyne–Duncan, ©1973.

*Primary Examiner*—J. Travis Brown
*Attorney, Agent, or Firm*—Connolly & Hutz

[57] ABSTRACT

Propyne compounds, which are capable of stabilizing photographic materials against fog, color fog and flattening of the gradation are disclosed. They may be added to emulsion layers and to processing baths.

8 Claims, No Drawings

PHOTOGRAPHIC MATERIAL CONTAINING A STABILIZING AGENT

This invention relates to a photographic material having at least one silver halide emulsion layer which has been improved by the addition of stabilizers capable of protecting the photographic material against the formation of fog and colour fog and against flattening of the gradation.

It is well known that materials which contain light sensitive silver halide emulsions, especially those which are chemically sensitized, tend to form fog due to the presence of nuclei which are capable of development without exposure. Such fogging occurs particularly during prolonged storage, especially at elevated temperatures and atmospheric moisture, excessively long development or development at excessively high temperatures or the presence of certain additives or excessive ripening of the emulsions.

It is known to add so called anti-fogging agents or stabilizers to photographic silver halide emulsions to prevent this fogging. Compounds which act as stabilizers include, for example, heterocyclic mercapto compounds such as those described in German Ausleges- chrift No. 1,183,371 and German Offenlegungsschriften Nos. 2,308,530 and 1,622,271.

These stabilizers however, have the disadvantage that, at effective concentrations, they generally reduce the sensitivity of the stabilized emulsion, thereby impairing its usefulness. They are also liable to have a deleterious effect on the gradation of the emulsion.

The stabilizers must meet various requirements with regard to their interaction with other photographic additives and in view of the multiplicity of photographic reproduction processes and the photographic materials employed for them, which the known stabilizers fail to do.

It is also known that colour images produced with the usual silver halide materials frequently show colour fogging or discolouration. The formation of a colour fog is due to the fact that the developer compounds are capable of being oxidized to a certain extent by the atmosphere and that the resulting oxidized developer compounds will also couple with the colour couplers in those areas of the photographic material in which no silver image was originally produced. This interfering oxidation of the developer may be caused not only by air but also by additives contained in the emulsions. Colour fogging and discolouration are found to occur mainly in those photographic recording materials in which couplers are incorporated in the light sensitive layers. Colour fogging and discolouration generally cannot be prevented by the methods normally used for stabilizing against silver fog.

The use of alkyl and dialkyl hydroquinone derivatives to stabilize against colour fog in colour photographic materials has been proposed in U.S. Pat. Nos. 2,403,721 and 2,701,197 and German Offenlegungsschrift No. 2,110,521.

These compounds, however, have the disadvantage that many of them can only be prepared by difficult processes comprising two to four stages and that some of them are not sufficiently resistant to diffusion so that in multilayered photographic materials they are liable to migrate from one layer to another, thereby producing undesirable side effects. The compounds partly crystallize before or during their application or they have an undesirable effect on the physical or chemical properties of the layers, one particularly disadvantageous effect being that some alkyl hydroquinones produce coloured side products by an oxidation reaction during application of the coating or development. These by-products cause discolouration of the photographic material, which is particularly undesirable in copying materials.

It is also known that colour reproduction can be improved by arranging an intermediate layer between the light sensitive silver halide emulsion layer and a layer containing the colour to suppress diffusion of the oxidation products of the developers into the layer containing the colour couplers. In order that the intermediate layer may perform this function, it contains inter alia compounds which react with the developer oxidation products to form colourless compounds. However, these so called "white couplers" do not prevent colour fogging sufficiently for practical purposes.

It is also known from German Pat. No. 2,304,321 to reduce discolouration by processing colour photographic materials in the presence of 2-propinyl thioether derivatives, but even this measure is no longer capable of satisfying the increased standards, especially for high temperature processing.

Lastly, it is known that flattening of the gradation may occur in photographic materials during storage, especially if the gradation is initially relatively steep. From U.S. Pat. No. 3,488,709, it is known that the gradation of emulsions which contain rhodium salts to steepen their gradation can be stabilized by the addition of cadmium salts. However, increasing importance is attached to avoiding the use of cadmium salts in photographic materials.

There is therefore still a need for stabilizers capable of stabilizing photographic materials against fogging, colour fogging and flattening of the gradation.

It is an object of the present invention to find stabilizers which are capable of stabilizing photographic materials against fogging, colour fogging and flattening of the gradation. It is another object of the invention to prepare photographic materials comprising at least one silver halide emulsion layer which are stabilized with these compounds.

The present invention relates to a photographic material having at least one silver halide emulsion layer and at least one stabilizing agent corresponding to the following formula I:

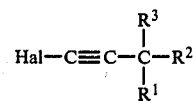

in which $R^1$ represents alkyl, in particular alkyl with 1 to 4 carbon atoms; aryl, in particular phenyl, which may be substituted, preferably with halogen or with a nitro, phenyl, phenoxy, alkyl, $CF_3O$ or $CF_3$ group; aralkyl; a heterocyclic group, for example pyridyl, in particular pyridyl-(4), pyridyl-(3) and pyridyl-(2);

$R^2$ represents hydroxyl or a heterocyclic group, in particular a group containing nitrogen and preferably having 5 or 6 ring atoms, for example 1-imidazolyl;

$R^3$ represents aryl, in particular phenyl which may be substituted with one or more substituents, in particular with an alkyl group having from 1 to 4 carbon atoms or with halogen or a nitro group;

Hal represents halogen, in particular Br or I; or a salt thereof.

The invention also relates to a process for the preparation of a photographic image by the processing of a photographic recording material in the presence of compounds to be used according to the invention.

The aforesaid alkyl, aryl and heterocyclic groups may contain further substituents which may in turn be substituted.

By "salts of compounds of formula I" are meant in particular those compounds in which the group $R^2$ is one corresponding to the following general formula and $X^-$ is the corresponding anion:

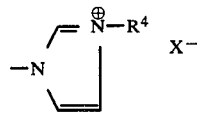

in which $R^4$ represents an alkyl or aralkyl group in particular an unsubstituted benzyl group or one which is substituted by a $C_1$ to $C_4$ alkyl or halogen on the aromatic ring, or hydrogen and $X^-$ represents halogen, in particular chlorine, bromine, or iodine, or an alkyl sulphate or an aryl sulphate anion, in particular a tosyl or mesyl group.

The following compounds of formulae II to IV have proved to be particularly suitable:

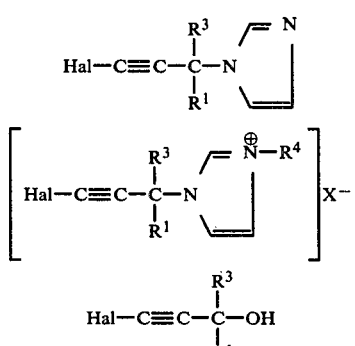

in which $R^1$ and Hal have the meaning specified under formula I, $R^3$ represents a phenyl group which may have one or more substituents and $R^4$ and $X^-$ have the meaning specified above.

Examples of compounds which may be used according to the invention are given in the following tables I and II:

TABLE I

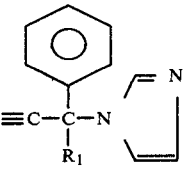

| Compound No. | Hal | $R^1$ | Melting point |
|---|---|---|---|
| 1 | Br | phenyl | 193° |

TABLE I-continued

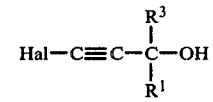

| Compound No. | Hal | $R^1$ | Melting point |
|---|---|---|---|
| 2 | I | phenyl | decomp. 199° |
| 3 | I | isopropyl | 159–160° |
| 4 | I | m-tolyl | 168–169° |
| 5 | Br | m-tolyl | 144–145.5° |

TABLE II $$Hal-C\equiv C-\underset{R^1}{\overset{R^3}{\underset{|}{\overset{|}{C}}}}-OH$$

| Compound Number | Hal | $R^1$ | $R^3$ | Melting point or refractive index | |
|---|---|---|---|---|---|
| 6 | Br | phenyl | phenyl | m.p: | 60–62° |
| 7 | I | phenyl | phenyl | m.p: | 106–07° |
| 8 | I | phenyl | p-nitrophenyl | m.p: | 116–18° |
| 9 | I | phenyl | o-fluorophenyl | m.p: | 81–82° |
| 10 | Br | phenyl | o-fluorophenyl | $n_D^{20}$ | 1.6040 |
| 11 | Br | 3-pyridyl | phenyl | m.p: | 107–08° |
| 12 | I | 4-pyridyl | phenyl | m.p: | decomp. 176° |
| 13 | Br | 4-pyridyl | phenyl | m.p: | 166–67° |
| 14 | I | 2-pyridyl | phenyl | m.p: | 86–87° |
| 15 | I | 4-pyridyl | p-tolyl | m.p: | decomp. 179–80° |
| 16 | Br | 4-pyridyl | p-tolyl | m.p: | decomp. 189° |
| 17+ 1 mol pyridine | Br | p-biphenylyl | o-chlorophenyl | m.p.: | 77–79° |
| 18 | I | p-biphenylyl | o-chlorophenyl | resinous | |
| 19 | Br | p-biphenylyl | m-chlorophenyl | m.p.: | 106–07° |
| 20 | I | p-biphenylyl | m-chlorophenyl | m.p.: | 99–100° |
| 21 | Br | p-biphenylyl | m-tolyl | m.p.: | 131–32° |
| 22 | I | p-biphenylyl | m-tolyl | m.p.: | 137–39° |
| 23 | Br | p-phenoxyphenyl | o-chlorophenyl | m.p.: | 95–96 |
| 24 | I | p-phenoxyphenyl | o-chlorophenyl | m.p.: | 104–05° |
| 25 | I | p-phenoxyphenyl | m-chlorophenyl | oil $n_D^{20}$ | 1.6272 |
| 26 | I | p-phenoxyphenyl | m-tolyl | m.p.: | 82–83° |
| 27 | Br | p-phenoxyphenyl | m-tolyl | oil $n_D^{40}$ | 1.6172 |
| 28 | I | phenyl | p-trifluoromethoxyphenyl | oil $n_D^{20}$ | 1.5697 |
| 29 | Br | phenyl | p-trifluoromethoxyphenyl | oil $n_D^{20}$ | 1.5427 |
| 30 | I | phenyl | 3-chloro-4-trifluoromethylphenyl | oil $n_D^{40}$ | 1.5860 |
| 31 | Br | phenyl | 3-chloro-4-trifluoromethylphenyl | oil $n_D^{40}$ | 1.5683 |
| 32 | I | phenyl | 2,6-difluorophenyl | m.p.: | 93–95° |
| 33 | Br | phenyl | 2,6-difluorophenyl | m.p.: | 60–61° |

TABLE II-continued $$\text{Hal}-C\equiv C-\underset{\underset{R^1}{|}}{\overset{\overset{R^3}{|}}{C}}-OH$$

| Compound Number | Hal | R¹ | R³ | Melting point or refractive index | |
|---|---|---|---|---|---|
| 34 | I | 3-pyridyl | p-tolyl | m.p.: | 148–50° |
| 35 | Br | 3-pyridyl | p-tolyl | m.p.: | decomp. 152° |
| 36 | I | phenyl | 2,4-difluorophenyl | oil $n_D^{20}$ | 1.6098 |
| 37 | Br | phenyl | 2,4-difluorophenyl | oil $n_D^{20}$ | 1.5845 |

The following quarternary salts of compound 2 are given as examples of salts of compounds corresponding to formula I:

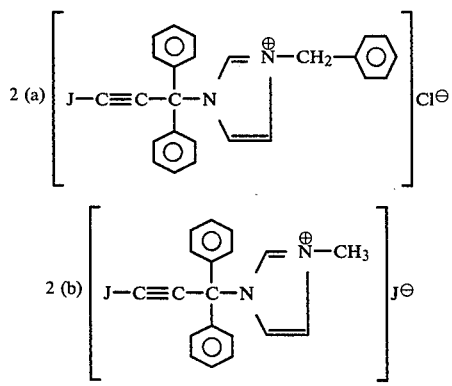

The compounds which are to be processed according to the invention may be prepared by the reaction of the corresponding propynes with halogen by methods which are well known in principle. The preparation of some of the compounds given in the tables is described below by way of example.

Preparation of compound No. 2:
3-iodo-1,1-diphenyl-1-(imidazolyl-1)-propyne

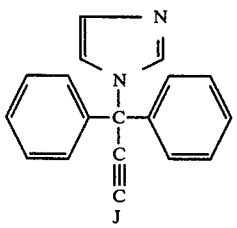

44.5 ml of 45% sodium hydroxide solution are added dropwise to 25.8 g (0.1 mol) of 1,1-diphenyl-1-(imidazolyl-1)-propyne in 200 ml of methanol at 20°–30° C. and 25.4 g (0.1 mol) of iodine are introduced portionwise at the same time. After one hour, 1000 ml of water are added to the reaction mixture. The crystals which have separated are suction-filtered and washed with water and then with hot acetonitrile. 26.8 g (69.8% of the theoretical yield) of 3-iodo-1,1-diphenyl-1-(imidazolyl-1)-propyne melting at 199° C. (decomposition) are obtained.

Preparation of compound No. 1:
3-bromo-1,1-diphenyl-1-(imidazolyl-1)-propyne

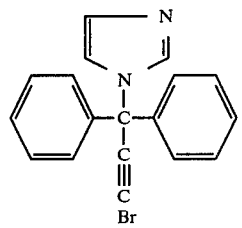

5.5 ml (0.11 mol) of bromine are added dropwise to 22 ml of concentrated sodium hydroxide solution in 50 ml of water at 0° to 5° C. 25.8 g (0.1 mol) of 1,1-diphenyl-1-(imidazolyl-1)-propyne dissolved in 100 ml of pyridine are gradually stirred into the resulting solution, the reaction temperature thereby rising to 40° C. Stirring is continued for 3 hours at room temperature, 1000 ml of water are then added and the crystals which have separated are suction-filtered and washed with acetonitrile and ether. 30.7 g (91% of the theoretical yield) of 3-bromo-1,1-diphenyl-1-(imidazolyl-1)-propyne melting at 193° C. are obtained.

Preparation of compound No. 7:
3-iodo-1,1-diphenyl-propyn-2-ol

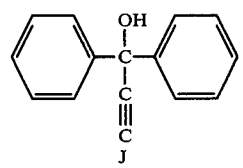

80 ml of concentrated sodium hydroxide solution are added dropwise to a solution of 41.6 g (0.2 mol) of 1,1-diphenyl-propyn-2-ol in 500 ml of methanol with cooling at 20° C. and 50.8 g (0.2 mol) of iodine are added portionwise at the same time. The reaction mixture is stirred for 3 hours at room temperature and filtered. 1000 ml of water are added portionwise to the filtrate. The colourless crystalline precipitate formed is suction-filtered, washed with water and dried. 53.5 g (80% of the theoretical yield) of 3-iodo-1,1-diphenyl-propyn-2-ol melting at 106°–107° C. are obtained.

Preparation of compound No. 21:
3-bromo-1-(3-tolyl)-1-(4-biphenylyl)-propyn-2-ol

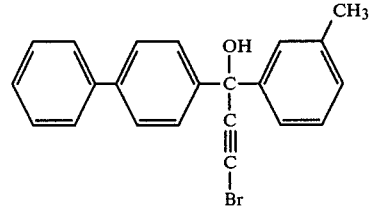

8.2 ml (0.16 mol) of bromine are added dropwise to 129 ml of 10% sodium hydroxide solution with stirring at 0°–5° C. 41.8 g (0.14 mol) of 1-(3-tolyl)-1-(4-biphenylyl)-propyn-2-ol dissolved in 150 ml of pyridine are stirred into this solution at 20° C. After 3 hours, the reaction mixture is poured into 1000 ml of water and the oil which separates is taken up with ethyl acetate. The organic phase is shaken several times with water, dehydrated over sodium sulphate, filtered and concentrated by evaporation at reduced pressure. The oil remaining behind is taken up in a small quantity of ether, and petroleum ether is added portionwise. The colourless crystals which separate are suction-filtered and dried. 34.8 g (65.9% of the theoretical yield) of 3-bromo-1-(3-tolyl)-1-(4-biphenylyl)-propyn-2-ol melting at 131° 132° C. are obtained.

Although a photographic material containing silver complexes of certain propynols which are substituted with alkyl or aryl groups has already been disclosed in German Offenlegungsschrift No. 2,159,631, these compounds are used in combination with certain sensitizers and are said to compensate for the loss in sensitivity due to addition of the sensitizer by a reduction in the pAg value. Fogging of the photographic materials, on the other hand, is considerably increased by the addition of these silver propynol complexes.

The usual silver halide emulsions are suitable for the present invention. The silver halide contained in them may be silver chloride, silver bromide or mixtures thereof, possibly with a small silver iodide content of up to 10 mol percent.

The materials prepared according to the invention may be developed with the usual colour developer substances, e.g the following:
N,N-dimethyl-p-phenylene diamine
4-amino-3-methyl-N-ethyl-N-methoxy ethylaniline
monomethyl-p-phenylene diamine
2-amino-5-diethylamino toluene
N-butyl-N-ω-sulphobutyl-p-phenylene diamine
2-amino-5-(N-ethyl-N-β-methane sulphonamidoethylamino)-toluene
N-ethyl-N-β-hydroxyethyl-p-phenylene diamine
N,N-bis-(β-hydroxyethyl)-p-phenylene diamine
2-amino-5-(N-ethyl-N-β-hydroxyethylamino)-toluene.

Other suitable colour developers have been described, for example, in J. Amer. Chem. Soc. 73, 3100 (1951).

The photographic material prepared according to the invention may contain the usual colour couplers, generally incorporated in the silver halide layers. The red sensitive layer, for example, contains a nondiffusible colour coupler for producing the cyan partial image, generally a phenol or α-naphthol coupler. The green sensitive layer contains at least one nondiffusible colour coupler for producing the magenta partial colour image, usually a 5-pyrazolone or indazolone colour coupler. The blue sensitive layer unit contains at least one non-diffusible colour coupler for producing the yellow partial image, generally a colour coupler having an open chain ketomethylene group. Large numbers of these colour couplers are known and have been described in numerous patent specifications. Examples may also be found in the publication entitled "Farbkuppler" by W. Pelz in "Mitteilungen aus den Forschungslaboratorien der Agfa, Leverkusen/Müchen", Vol. III (1961) and K. Venkataraman in "The Chemistry of Synthetic Dyes", Vol. 4, 341 to 387 Academic Press, 1971.

2-equivalent couplers may also be used as non-diffusible colour couplers. These contain a removable substituent in the coupling position so that they only require two equivalents of silver halide for formation of the colour, in contrast to the usual 4-equivalent couplers. Suitable 2-equivalent couplers include, for example, the known DIR couplers in which the removable group is released as a diffusible development inhibitor after the reaction with colour developer oxidation products. So called white couplers may also be used to improve the properties of the photographic material.

The non-diffusible colour couplers and colour producing compounds are added to the light sensitive silver halide emulsions or other casting solutions by the usual known methods. If they are water soluble or alkali soluble compounds, they may be added to the emulsions in the form of aqueous solutions, to which water miscible organic solvents such as ethanol, acetone or dimethyl formamide may be added. If the non-diffusible colour couplers and colour producing compounds used are insoluble in water or alkalis, they may be emulsified in the usual manner, for example by mixing a solution of the compounds in a low boiling organic solvent either directly with the silver halide emulsion or first with an aqueous gelatine solution and then removing the organic solvent in the usual manner and mixing the resulting emulsion of the compound in gelatine with the silver halide emulsion. So-called coupler solvents or oil formers may also be used to emulsify such hydrophobic compounds. These oil formers or coupler solvents are generally organic compounds with a relatively high boiling point in which the non-diffusible colour couplers and development inhibitor releasing compounds which are required to be emulsified in the silver halide emulsions become enclosed in the form of oily droplets. Information on this may be found, for example, in U.S. Pat. Nos. 2,322,027; 2,533,514; 3,689,271; 3,764,336 and 3,765,897.

The binder used for the photographic layers is preferably gelatine but this may be partly or completely replaced by other natural or synthetic binders. Examples of suitable natural binders include alginic acid and its derivatives such as its salts, esters or amides, cellulose derivatives such as carboxymethyl cellulose, alkyl celluloses such as hydroxyethyl cellulose, starches or their derivatives such as ethers or esters, and carragheenates. Among suitable synthetic binders may be mentioned polyvinyl alcohol, partially saponified polyvinyl acetate and polyvinyl pyrrolidone.

The emulsions may also be chemically sensitized, for example by the addition of sulphur-containing compounds such as allyl isothiocyanate, allyl-thiourea, and sodium thiosulphate at the chemical ripening stage. Reducing agents may also be used as chemical sensitizers, e.g. the tin compounds described in Belgian Pat. No. 493,464 or No. 568,687, or polyamines such as diethylene triamine or aminomethyl sulphinic acid derivatives, e.g. according to Belgian Pat. No. 547,323.

Noble metals such as gold, platinum, palladium, iridium, ruthenium or rhodium and compounds of these metals may also be used as chemical sensitizers. This method of chemical sensitization has been described in the article by R. Koslowsky, Z. Wiss. Phot. 46, 65–72 (1951).

The emulsions may also be sensitized with polyalkylene oxide derivatives, e.g. with a polyethylene oxide having a molecular weight of from 1,000 to 20,000, or with condensation products of alkylene oxides and aliphatic alcohols, glycols, cyclic dehydration products of hexitols, alkyl substituted phenols, aliphatic carboxylic acids, aliphatic amines, aliphatic diamines and amides. The condensation products have a molecular weight of at least 700, preferably more than 1,000. These sensitizers may, of course, be combined to produce special effects, as described in Belgian Pat. No. 537,278 and British Pat. No. 727,982.

The emulsions may also be optically sensitized, e.g. with the usual polymethine dyes such as neutrocyanines, basic or acid carbocyanines, rhodacyanines hemicyanines, styryl dyes and oxonoles. Sensitizers of this type have been described in the work by F. M. Hamer entitled "The Cyanine Dyes and related Compounds", (1964).

The emulsions may contain the usual stabilizers, e.g. homopolar compounds or salts of mercury which have aromatic or heterocyclic rings, such as mercapto triazoles, or simple mercury salts, sulphonium mercury double salts and other mercury compounds. Azaindenes are also suitable stabilizers, especially tetra and pentaazaindenes and in particular those which are substituted with hydroxyl or amino groups. Compounds of this type have been described in the article by Birr. Z. Wiss. Phot. 47 (1952) pages 2 to 58. Other suitable stabilizers include heterocyclic mercapto compounds, e.g. phenyl mercapto tetrazole, quaternary benzothiozole derivatives and benzotriazole.

The emulsions may be hardened in the usual manner, for example with formaldehyde or halogen substituted aldehydes which contain a carboxyl group, such as mucobromic acid, diketones, methane sulphonic acid esters and dialdehydes.

The photographic layers may also be hardened with hardeners of the epoxide type of the heterocyclic ethylene imine or acryloyl type. Examples of such hardeners have been described e.g. in German Offenlegungsschrift No. 2,263,602 and in British Pat. No. 1,266,655. The layers may also be hardened by the process according to German Offenlegungsschrift No. 2,218,009 to produce colour photographic materials which are suitable for high temperature processing.

The photographic layers or colour photographic multilayered materials may also be hardened with diazine, triazine or 1,2-dihydroquinoline hardeners as described in British Pat. Nos. 1,193,290; 1,251,091; 1,306,544 and 1,266,655, French Pat. No. 7,102,716 and U.K. Pat. No. 1,452,669. Examples of such hardeners include diazine derivatives containing alkyl sulphonyl or aryl sulphonyl groups, derivatives of hydrogenated diazines or triazines, e.g. 1,3,5-hexahydrotriazine, fluoro substituted diazine derivatives such as fluoropyrimidine, and esters of 2-substituted 1,2-dihydroquinoline- or 1,2-dihydroisoquinoline-N-carboxylic acids. Vinyl sulphonic acid hardeners and carbodiimide or carbamoyl hardeners of the type described e.g. in German Offenlegungsschriften Nos. 2,263,602; 2,225,230 and 1,808,685, French Pat. No. 1,491,807, German Pat. No. 872,153 and DDR Pat. No. 7218 may also be used. Other suitable hardeners have also been described for example in British Pat. No. 1,268,550.

The stabilizers according to the invention are preferably added to the light sensitive silver halide emulsions after chemical ripening. The stabilizers, may, of course, also be added to other photographic layers. The concentration of the stabilizers in the emulsion may vary within wide limits and depends mainly on the nature of the emulsion and the desired effect. Quantities of from 20 mg to 3 g, in particular from 50 to 2,500 mg per mol of silver halide generally produce the desired effects. In black and white emulsions it is preferred to use quantities of from 50 to 2,500 mg and in emulsions containing colour couplers quantities of from 200 to 2,500 mg of stabilizer per mol of silver halide. The optimum quantity to be added can easily be determined for each emulsion by means of the usual tests.

The stabilizers to be used according to the invention may also be added to one of the baths used for processing the photographic materials, for example a short stop bath or an after treatment bath. The stabilizers are used in baths at concentrations of from 0.4 g/l to 2 g/l, preferably from 0.5 g/l to 1.5 g/l.

The following examples serve to explain the invention but do not restrict the invention to the embodiments given in the examples.

EXAMPLE 1

A silver bromide emulsion containing 14 mol percent of silver chloride and 1 mol percent of silver iodide for producing a copying paper with a hard gradation is prepared in the usual manner with the addition of sodium hexachlorohodinate, ripened to optimum sensitivity with the sulphur sensitizers and washed. The ratio of gelating to silver in the finished emulsion is 3.6:1, the pH 5.7.

The emulsion is sensitized with 25 ml per kg of emulsion of a 0.1% aqueous solution of optical sensitizer corresponding to the following formula:

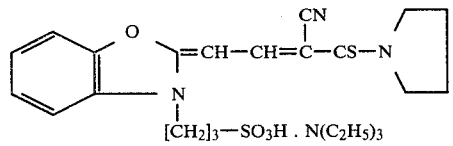

The sensitized emulsion is then divided into several equal parts and stabilizers entered in the following table are added to the individual parts in the quantities given, dissolved in methanol.

Before each sample is cast on a substrate of baryte paper, 20 ml of a 5% aqueous solution of saponin and 0.75 ml of a 30% aqueous solution of formaldehyde per kg of emulsion are added to it. The quantity of silver applied calculated as silver nitrate amounts to 2.7 g of $AgNO_3/m^2$. A protective layer having the following composition is applied to the emulsion layer:

20 g of gelatine
1 liter of water
2.4 ml of a 30% aqueous formaldehyde solution
7.5 ml of a 5% aqueous saponin solution.

The samples are exposed behind a $\sqrt[4]{2}$ step wedge both when freshly prepared and after 9 months storage at room temperature and developed for 90 seconds at 20° C. in developer I having the composition given below. The samples are then fixed and washed in the usual manner.

| Developer I | |
| --- | --- |
| p-methylaminophenol-sulphate | 1 g |
| sodium sulphite sicc. | 13 g |
| hydroquinone | 3 g |
| sodium carbonate sicc. | 26 g |
| potassium bromide | 1 g |
| made up with water to 1 liter. | |

As the data summarised in Table 3 show, excellent stabilization of the gradation and in most cases also reduction in fogging are achieved in the materials according to the invention.

The table also gives values for the "long time fog" at high temperature processing. These are obtained on unexposed materials which are otherwise processed in the same manner but developed for 2 minutes or 4 minutes at 30° C. instead of for 90 seconds at 20° C. It can be seen from the table that some of the materials according to the invention have a substantially lower long term fog than the unstabilized material.

Comparison substance A is a conventional stabilizer containing mercapto groups, i.e. p-[3-(2-mercapto-3,4-dihydro-4]-keto-quinazolinyl)-benzene sulphonic acid. This compound is known as anti-fogging agent from German Offenlegungsschrift No. 1,962,605 and functions as anti-fogging agent, as can be seen from table 3, but is not capable of stabilizing the sensitivity or the gradation.

EXAMPLE 1

TABLE 3

| | | Sensitivity: γ stage at density 1 | | | | | | | | |
|---|---|---|---|---|---|---|---|---|---|---|
| | | Examination of fresh sample | | | | | re-examination after 9 months | | | |
| | | | | | Long-term fog | | | | | long-term fog |
| Compound No. | mg/kg | sensitivity | γ | fog | 2 min | 4 min | sensitivity | γ | fog | 2 min | 4 min |
| Control sample | — | 16.9 | 5.1 | 0.06 | 0.08 | 0.18 | 19.1 | 3.7 | 0.07 | 0.10 | 0.20 |
| 1 | 131 | 16.0 | 5.2 | 0.06 | 0.07 | 0.10 | 16.0 | 4.9 | 0.07 | 0.07 | 0.12 |
| 3 | 68 | 15.8 | 5.7 | 0.06 | 0.06 | 0.12 | 16.0 | 6.1 | 0.08 | 0.08 | 0.13 |
| 8 | 73 | 16.0 | 4.8 | 0.06 | 0.07 | 0.16 | 15.5 | 5.1 | 0.08 | 0.09 | 0.19 |
| 8 | 147 | 14.5 | 5.6 | 0.06 | 0.07 | 0.16 | 14.9 | 5.7 | 0.07 | 0.09 | 0.18 |
| 12 | 130 | 16.4 | 5.5 | 0.06 | 0.07 | 0.15 | 16.8 | 4.9 | 0.07 | 0.08 | 0.19 |
| 19 | 385 | 16.2 | 4.8 | 0.06 | 0.07 | 0.15 | 16.8 | 4.7 | 0.07 | 0.08 | 0.18 |
| 20 | 430 | 16.3 | 5.3 | 0.04 | 0.07 | 0.14 | 17.3 | 4.8 | 0.05 | 0.08 | 0.18 |
| A | 30 | 16.5 | 5.2 | 0.04 | 0.08 | 0.11 | 18.6 | 3.9 | 0.05 | 0.08 | 0.11 |

EXAMPLE 2

A high sensitivity silver iodobromide emulsion containing 5 mol percent of iodide and having a gelatine: silver ratio of 1.2 and a silver nitrate content of 85 g per kg of emulsion was ripened to optimum sensitivity with sulphur and gold compounds.

The emulsion mixture was sub-divided into several parts and the following compounds were added per kg of emulsion:

| | |
|---|---|
| 4-hydroxy-6-methyl-1,3,3a,7-tetraazaindene as 1% aqueous alkaline solution | 200 mg |
| saponin 10% solution in water | 600 mg |
| formalin 10% solution in water | 10 ml | and the substances according to the invention (1% dissolved in methanol) shown in the following table in the quantities indicated. The quantities were not sufficient to produce significant reduction in the sensitivity.

The emulsions were then cast on a cellulose acetate substrate and dried (application 7.0 to 7.2 g calculated as silver nitrate per m²). The samples were tested while fresh and after 3 days storage in a heating cupboard at 60° C.

They were then exposed behind a grey wedge in a sensitometer and developed for 16 minutes at 20° C. in developer II of the following composition:

| Developer II | |
|---|---|
| Sodium sulphite sicc. | 50 g |
| Borax | 15 g |
| hydroquinone | 6 g |
| 1-phenyl-2-pyrazolidone | 0.5 g |
| potassium bromide | 2 g | made up with water to 1 liter.

This is followed by a short stop bath consisting of 10 g of sodium acetate sicc. and 20 g of 96% glacial acetic acid in 1 liter of water. The emulsions are then fixed with 15% ammoniumthiosulphate and 1% sodium sulphite solution and washed. The results of sensitometric examination are shown in Table 4.

The advantageous effect of some of the substances according to the invention becomes very clear when one considers the behaviour of the photographic material when developed at an elevated temperature in a developer containing silver complex formers which is a typical black and white developer used for reversal processing of photographic materials. For this purpose, an unexposed sample is developed in developer III for 3, 6 and 9 minutes at 38° C.

| Developer III | |
|---|---|
| 1-phenyl-3-pyrazolidone | 0.3 g |
| hydroquinone | 6.0 g |
| sodium carbonate sicc. | 35.0 g |
| sodium sulphite sicc. | 50.0 g |
| potassium thiocyanate sicc. | 2.5 g |
| potassium bromide | 2.0 g |
| ethylene diamino-N,N,N',N'-tetraacetic acid, Na$_4$ salt | 2.0 g |
| made up with water to 1 liter and adjusted to pH 10.0 ± 0.1. | |

Further processing is carried out as indicated above. The degree of fogging is given in table 4 in terms of "percentage fogging" which is obtained by dividing the developed silver (as silver nitrate) by silver (as silver nitrate) before processing and multiplying this ratio by 100. The result given is the mean value of the developed silver from 3 development times.

The table shows that the substances reduce fogging, particularly the fogging in the heating cupboard, and that substances Nos. 3 and 8 in particular reduce fogging in developer III and are therefore suitable antifogging agents for reversal materials.

Comparison substance B is 3-mercapto-1,2,4-triazole and comparison substance C is 3-mercapto-5-acetylamino-1-phenyl-1,2,4-triazole which is described as stabilizer in German Offenlegungsschrift No. 2,308,530. Although these substances are capable of reducing fogging to a certain extent when processing is carried out in developer II, substance B at the same time causes a distinct loss in sensitivity. The comparison substances have virtually no fog reducing effect in developer III.

TABLE 4

| Compound No. | mg/kg | Developer II | | | | | | Developer III percentage fogging after storage in heating cupboard |
|---|---|---|---|---|---|---|---|---|
| | | Fresh sample | | | Heating cupboard sample | | | |
| | | Sensitivity* | γ | fog | Sensitivity* | γ | fog | |
| Control sample | — | standard | 0.85 | 0.11 | standard | 0.86 | 0.15 | 34 |
| 3 | 35 | −1° | 0.85 | 0.10 | −0.8° | 0.86 | 0.09 | 20 |
| 8 | 367 | −0.2° | 0.87 | 0.09 | +0.9° | 0.89 | 0.09 | 21 |
| 9 | 352 | ±0° | 0.86 | 0.11 | +0.7° | 0.88 | 0.13 | 27 |
| 12 | 325 | −1.0° | 0.84 | 0.10 | −0.5° | 0.86 | 0.12 | 25 |
| 15 | 140 | −0.4° | 0.86 | 0.11 | −0.2° | 0.81 | 0.12 | 28 |
| B | 25 | −2.0° | 0.71 | 0.10 | −2.5° | 0.68 | 0.13 | 32 |
| C | 56 | ±0° | 0.75 | 0.10 | −0.5° | 0.76 | 0.11 | 33 |

*3° = 1 shutter stop

EXAMPLE 3

30 g of an alkali soluble yellow coupler corresponding to the following formula

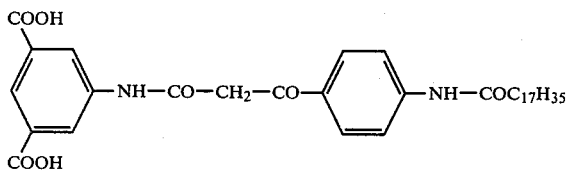

were added in the form of a solution in aqueous-methanolic soda to 1 kg of a blue sensitized silver iodobromide emulsion containing 0.24 mol of silver halide (consisting of silver bromide containing 1 mol percent of silver iodide). The pH of the emulsion was then adjusted to 6.7 and 1 g of saponin dissolved in water was added as wetting agent and 0.2 g of 4-hydroxy-6-methyl-1,3,3a,7-tetraazaindene in aqueous alkaline solution and 1 g of 1,3,5-triacrylohexahydro-1,3,5-triazine in methanolic solution as hardener and the resulting emulsion was divided into several equal parts. The compounds according to the invention shown in the following table were added to the individual parts in the quantities indicated, which were chosen so that as far as possible the sensitivity was unaffected.

The samples of emulsion were cast on corona irradiated polyethylene coated paper in amounts corresponding to a silver application of 0.75 g of AgNO$_3$/m$^2$. Each emulsion layer was covered with a 2% gelatine solution to which 0.3 g liter of 1,3,5-triacrylo-hexahydro-1,3,5-triazine in methanolic solution had been added, the gelatine layer containing 2 g of gelatine/m$^2$.

After drying, the material were exposed behind a step wedge and developed for 110 seconds at 35° C. in developer IV of the following composition.

| Developer IV | |
|---|---|
| trisodium salt of nitrilotriacetic acid | 2 g |
| sodium sulphite sicc. | 3 g |
| potassium bromide | 0.4 g |
| potassium carbonate | 35 g |
| benzyl alcohol | 5 ml |
| hydroxylamine hydrochloride | 3 g |
| N-butyl-N-ω-sulphobutyl-p-phenylene diamine | 6 g |
| made up with water to 1 liter. | |

The following baths are used in subsequent processing:

| Short stop baths: | buffer solution of sodium acetate and acetic acid adjusted to pH 6.5. |
|---|---|
| Bleach fixing bath: | |
| 10 g | of Na$_4$ salt of ethylene diamino-N,N,N',N'-tetracetic acid, |
| 2 g | sodium sulphite sicc., |
| 40 g | sodium-iron-(III) salt of ethylene diamino-tetracetic acid, |
| 13 g | disodium phosphate, |
| 100 g | ammoniumthiosulphate |
| made up with water to 1 liter and adjusted to pH 7.2. | |

The processing times after development are as follows:

| Short stop bath | 1 minute |
|---|---|
| washing | 1 minute |
| bleach fixing | 3 minutes |
| washing | 3 minutes |

Yellow images of the step wedge are obtained. To determine the "long term fog", unexposed samples are subjected to the same process but developed for 165 seconds.

As seen from the results summarized in table 5, the compounds reduce the colour fog, especially when the development time is prolonged.

Comparison substance D is 2-amino-5-propyn-(2)-yl-thio-1,3,4-thiadiazole known as anti-fogging agent from German Offenlegungsschrift No. 2,304,321. Comparison substance D is less effective than the substances according to the invention in reducing the fog, and especially in reducing the long term fog, and it suppresses the sensitivity and flattens the gradation even at relatively low concentrations.

TABLE 5

| Compound No. | mg/kg | Developer IV | | | | |
|---|---|---|---|---|---|---|
| | | Sensitivity* | gradation | D$_{max}$ | fog | long term fog |
| Control sample | — | 18.5 | 2.54 | 1.75 | 0.22 | 0.28 |
| 1 | 326 | 18.8 | 2.68 | 1.78 | 0.07 | 0.08 |
| 3 | 204 | 18.1 | 2.49 | 1.76 | 0.08 | 0.09 |
| 7 | 324 | 18.6 | 2.48 | 1.77 | 0.13 | 0.11 |
| 8 | 367 | 18.3 | 2.45 | 1.75 | 0.08 | 0.14 |
| 9 | 176 | 18.6 | 2.56 | 1.78 | 0.11 | 0.14 |
| 12 | 325 | 18.0 | 2.51 | 1.73 | 0.18 | 0.16 |
| 14 | 325 | 18.4 | 2.63 | 1.73 | 0.13 | 0.15 |
| 17 | 185 | 17.9 | 2.45 | 1.77 | 0.08 | 0.11 |
| 19 | 385 | 17.9 | 2.58 | 1.75 | 0.10 | 0.16 |
| 21 | 146 | 18.0 | 2.43 | 1.75 | 0.08 | 0.11 |

TABLE 5-continued

| | | | Developer IV | | | |
|---|---|---|---|---|---|---|
| Compound No. | mg/kg | Sensitivity* | gradation | $D_{max}$ | fog | long term fog |
| 22 | 164 | 18.0 | 2.54 | 1.76 | 0.09 | 0.10 |
| 24 | 446 | 18.6 | 2.53 | 1.78 | 0.12 | 0.13 |
| Comparison experiment | | | | | | |
| D | 20 | 18.0 | 2.44 | 1.74 | 0.17 | 0.20 |
| D | 60 | 17.6 | 2.31 | 1.71 | 0.15 | 0.18 |

*Sensitivity = x stages at density 1

EXAMPLE 4

The advantageous effect of the substances to be used according to the invention becomes particularly clear when they are used for the development of the photographic material in the presence of sodium thiosulphate. In practice, development in the presence of thiosulphate occurs due to migration of the developer substance into the fixing bath or into the bleach fixing bath, especially in rapid processes in which no short stop bath is used between the developer and fixing or bleach fixing bath, as well as due to migration of sodium thiosulphate into the developer, e.g. via clamps and other parts of the apparatus. This causes severe fogging in the usual photographic materials but when the photographic material according to the invention is developed with developer V containing thiosulphate, the fog is drastically reduced, as can be seen from table 6. The compound used as comparison substance D is the same as in Example 3. The material is similar to that described in Example 3 to which the substances used according to the invention are added in the quantities indicated in table 6.

| Developer V | |
|---|---|
| N-butyl-N-ω-sulphobutyl-p-phenylene diamine | 5 g |
| hydroxylamine hydrochloride | 2.7 g |
| sodium sulphite sicc. | 3 g |
| nitrilotriacetic acid trisodium salt | 2 g |
| potassium carbonate | 75 g |
| potassium bromide | 1 g |
| sodium thiosulphate | 1 g |
| made up with water to 1 liter. | |

Employing otherwise the same process as in Example 3, unexposed material is developed for 2 minutes at 25° C. in developer V instead of developer IV.

TABLE 6

| Compound No. | mg/kg | Fog |
|---|---|---|
| / | / | 0.34 |
| D | 20 | 0.29 |
| D | 60 | 0.27 |
| 1 | 326 | 0.07 |
| 3 | 136 | 0.05 |
| 7 | 324 | 0.02 |
| 8 | 367 | 0.08 |
| 12 | 325 | 0.04 |
| 14 | 325 | 0.11 |
| 20 | 430 | 0.12 |
| 22 | 164 | 0.14 |
| 24 | 446 | 0.07 |

The comparison substance hardly reduces the fog.

EXAMPLE 5

A colour photographic multilayered material A containing a blue sensitized, a green sensitized and a red sensitized layer and a gelatine separating layer between each of the emulsion layers is prepared on a corona irradiated polyethylene coated paper substrate, 320 mg of compound 12 in the form of a 1% methanolic solution previously having been added per mol of silver halide to the emulsions ready for casting the blue sensitive yellow layer and the green sensitive magenta layer.

A similar colour photographic multilayered material B was prepared as comparison material in which the emulsions contained none of the compounds according to the invention.

The resulting colour photographic multilayered material was exposed in a conventional sensitometer behind a test image containing a grey, a blue, a green and a red step wedge.

Development was carried out for 110 seconds at 35° C. in the following developer VI:

| | |
|---|---|
| 5 g | N-butyl-N-ω-sulphobutyl-p-phenylene diamine. |
| 1.2 g | hydroxylamine hydrochloride, |
| 2 g | sodium sulphite sicc. |
| 2 g | sodium metaphosphate, |
| 75 g | potassium carbonate, |
| 1 g | potassium bromide, |
| made up with water to 1 liter. | |

Subsequent processing comprises the following baths: Short stop bath: a buffer solution of sodium acetate and acetic acid adjusted to pH 6.5;

Bleach fixing bath:

10 g of sodium salt of ethylene diaminotetracetic acid, 2 g of sodium sulphite, sicc.

40 g of sodium-iron (III) salt of ethylene diaminotetracetic acid, 13 g of disodium phosphate, 100 g of ammonium thiosulphate, made up with water to 1 liter and adjusted to pH 7.0.

The processing times after development are as follows:

1 minute short stop bath, 1 minute washing, 5 minutes bleach fixing bath, 10 minutes washing.

After exposure and processing, a comparison of the sensitometric results showed that the colour photographic multilayered material A containing the compound according to the invention and the comparison material B had the same sensitivity, the same gradation and the same maximum density. A comparison of the minimum densities is shown in the following table:

| | Minimum Density | | |
|---|---|---|---|
| Sample | Yellow | Magenta | Cyan |
| A | 0.14 | 0.12 | 0.10 |
| B | 0.16 | 0.18 | 0.10 |

We claim:

1. Light sensitive color photographic material having at least one silver halide emulsion layer of improved stability said material having associated with said silver halide layer at least one stabilizing compound, wherein the improvement comprises a stabilizing compound of the following general formula:

$$\text{Hal}-\text{C}\equiv\text{C}-\underset{\underset{R^1}{|}}{\overset{\overset{R^3}{|}}{\text{C}}}-R^2$$

in which
- $R^1$ represents an alkyl, aralkyl or pyridyl group, or aryl which may be substituted with halogen or with a nitro, phenyl, phenoxy, alkyl, $CF_3O$ or $CF_3$ group;
- $R^2$ represents a hydroxyl group, or an imidazolyl group;
- $R^3$ represents an aryl group, which may be substituted with an alkyl group having from 1-4 carbon atoms or with halogen or with a nitro group;
- Hal represents halogen or a salt thereof, in an amount effective for stabilization of the silver halide.

2. Light sensitive photographic material according to claim 1, in which $R^2$ represents an imidazolyl-(1)-group or a group corresponding to the following general formula:

$$-N\diagup\hspace{-1em}\diagdown\overset{\oplus}{N}-R^4$$

and in which
- $R^4$ represents alkyl, aralkyl or hydrogen and
- X represents halogen, alkylsulphate or arylsulphate.

3. Light sensitive photographic material according to claim 1, in which the stabilizer corresponds to the following general formula:

$$\text{Hal}-\text{C}\equiv\text{C}-\underset{\underset{R^1}{|}}{\overset{\overset{R^3}{|}}{\text{C}}}-\text{OH}$$

in which
- $R^1$ has the meaning specified above and
- $R^3$ represents a phenyl group which may be substituted once or more than once and
- Hal represents bromine or iodine.

4. Light sensitive photographic material according to claim 1 in which $R^1$ represents alkyl with 1 to 4 carbon atoms; phenyl or a phenyl group substituted with at least one $CF_3O$, $CF_3$, nitro, phenyl, phenoxy or alkyl group or halogen; or a pyridyl-(4), pyridyl-(3) or pyridyl-(2) group.

5. Light sensitive photographic material according to claim 1 in which at least one compound as a stabilizer selected from the group consisting of:

(a) I—C≡C—C(phenyl)(phenyl)—N(imidazole)

(b) [structure with NO₂-phenyl, I—C≡C—C(OH)—phenyl, phenyl, J—C≡C—C(OH)—piperidinyl, Cl-phenyl, J—C≡C—C(OH)—phenyl-O-phenyl]

6. Light sensitive photographic material according to claim 1 containing the stabilizer in a quantity of from 20 to 3,000 mg per mol of silver halide.

7. Light sensitive photographic material according to claim 1 containing at least one azaindene stabilizer.

8. In a process for the production of photographic images by imagewise exposure of photographic material which contains at least one silver halide emulsion layer, development and stabilization of the silver halide, the improvement according to which development is carried out with a composition containing in a stabilizing amount at least one compound corresponding to the following formula or a salt thereof:

$$\text{Hal}-\text{C}\equiv\text{C}-\underset{\underset{R^1}{|}}{\overset{\overset{R^3}{|}}{\text{C}}}-R^2$$

in which
- $R^1$ represents an alkyl, aralkyl or pyridyl group or aryl which may be substituted with halogen or with a nitro, phenyl, phenoxy, alkyl, $CF_3O$ or $CF_3$ group;
- $R^2$ represents a hydroxyl group or an imidazolyl group;
- $R^3$ represents an aryl group, which may be substituted with an alkyl group having from 1-4 carbon atoms or with halogen or with a nitro group,
- Hal represents halogen or a salt thereof, in an amount effective for stabilization of the silver halide.

* * * * *